US011801488B2

(12) United States Patent
Keum et al.

(10) Patent No.: US 11,801,488 B2
(45) Date of Patent: Oct. 31, 2023

(54) METHOD OF PREPARING ALUMINA CATALYST, ALUMINA CATALYST PREPARED USING SAME, AND METHOD OF PREPARING PROPYLENE USING ALUMINA CATALYST

(71) Applicant: LG CHEM, LTD., Seoul (KR)

(72) Inventors: Young Sub Keum, Daejeon (KR); Dae Heung Choi, Daejeon (KR); Joo Young Cheon, Daejeon (KR); Hyeon Bin Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 320 days.

(21) Appl. No.: 17/425,670

(22) PCT Filed: Nov. 17, 2020

(86) PCT No.: PCT/KR2020/016120
§ 371 (c)(1),
(2) Date: Jul. 23, 2021

(87) PCT Pub. No.: WO2021/256628
PCT Pub. Date: Dec. 23, 2021

(65) Prior Publication Data
US 2022/0314197 A1 Oct. 6, 2022

(30) Foreign Application Priority Data
Jun. 19, 2020 (KR) .................. 10-2020-0074931

(51) Int. Cl.
*B01J 20/08* (2006.01)
*C07C 1/24* (2006.01)
*B01J 37/10* (2006.01)
*C01F 7/021* (2022.01)

(52) U.S. Cl.
CPC ............... *B01J 20/08* (2013.01); *B01J 37/10* (2013.01); *C01F 7/021* (2013.01); *C07C 1/24* (2013.01); *C07C 2521/04* (2013.01)

(58) Field of Classification Search
CPC ... B01J 20/08; B01J 37/08; B01J 37/10; B01J 35/002; B01J 35/1014; B01J 35/1042;
(Continued)

(56) References Cited

U.S. PATENT DOCUMENTS

| 4,016,067 A | * | 4/1977 | Fischer | ................... B01J 35/10 |
| | | | | 208/89 |
| 5,227,563 A | | 7/1993 | Fukuhara et al. | |

(Continued)

FOREIGN PATENT DOCUMENTS

| CN | 1649672 A | 8/2005 |
| CN | 101580461 A | 11/2009 |

(Continued)

OTHER PUBLICATIONS

Jakrapan Janlamool et al., "Catalytic Ethanol Dehydration to Ethylene Over Nanocrystalline x-and y-Al2O3 Catalysts", J. Oleo Sci., vol. 66, No. 9, pp. 1029-1039 (2017).

*Primary Examiner* — Youngsul Jeong
*Assistant Examiner* — Jason Y CHong
(74) *Attorney, Agent, or Firm* — Bryan Cave Leighton Paisner LLP

(57) ABSTRACT

A method of preparing an alumina catalyst including: performing primary calcination of an alumina precursor at a primary calcination temperature to form a mixed-phase alumina including 1% to 15% by weight of alpha-alumina, 60% to 95% by weight of theta-alumina, and 4% to 25% by weight of delta-alumina; steam-treating the mixed-phase alumina with water vapor at a steam-treating temperature lower than the primary calcination temperature to form
(Continued)

activated mixed-phase alumina; and performing secondary calcination of the activated mixed-phase alumina at a secondary calcination temperature higher than the steam treatment temperature and lower than the primary calcination temperature after step S2. An alumina catalyst prepared using the method, and a method of preparing propylene using the alumina catalyst.

10 Claims, 2 Drawing Sheets

(58) Field of Classification Search
CPC ........... B01J 21/04; C01F 7/021; C01F 7/441; C07C 1/24; C07C 2521/04; C07C 5/48; C07C 11/06; C07C 2527/125; Y02P 20/52
See application file for complete search history.

(56) References Cited

U.S. PATENT DOCUMENTS

| | | |
|---|---|---|
| 5,475,183 A | 12/1995 | Araki et al. |
| 10,010,877 B2 | 7/2018 | Jothimurugesan et al. |
| 2005/0033101 A1 | 2/2005 | Voskoboynikov et al. |
| 2010/0068130 A1* | 3/2010 | Wilhelm .................. C01B 3/40 427/372.2 |

FOREIGN PATENT DOCUMENTS

| | | |
|---|---|---|
| CN | 102416325 A | 4/2012 |
| CN | 109529811 A | 3/2019 |
| CN | 110354837 A | 10/2019 |
| EP | 3092211 B1 | 6/2017 |
| JP | S55-116623 A | 9/1980 |
| JP | H03-127745 A | 5/1991 |
| JP | 2003-531712 A | 10/2003 |
| JP | 2014-181201 A | 9/2014 |
| KR | 10-1997-0009880 A | 3/1997 |
| KR | 10-2004-0065270 A | 7/2004 |
| KR | 10-1527845 B1 | 6/2015 |
| KR | 10-2019-0093379 A | 8/2019 |
| WO | 2015/170686 A1 | 11/2015 |
| WO | 2019229061 A1 | 12/2019 |

* cited by examiner

[FIG. 1A]
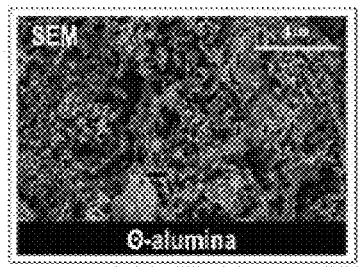
[FIG. 1B]
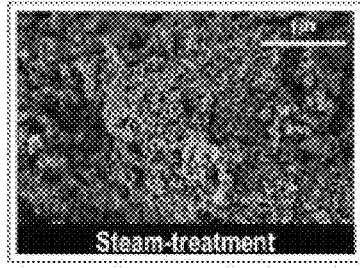
[FIG. 1C]
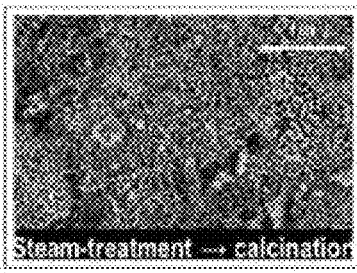
[FIG. 2]
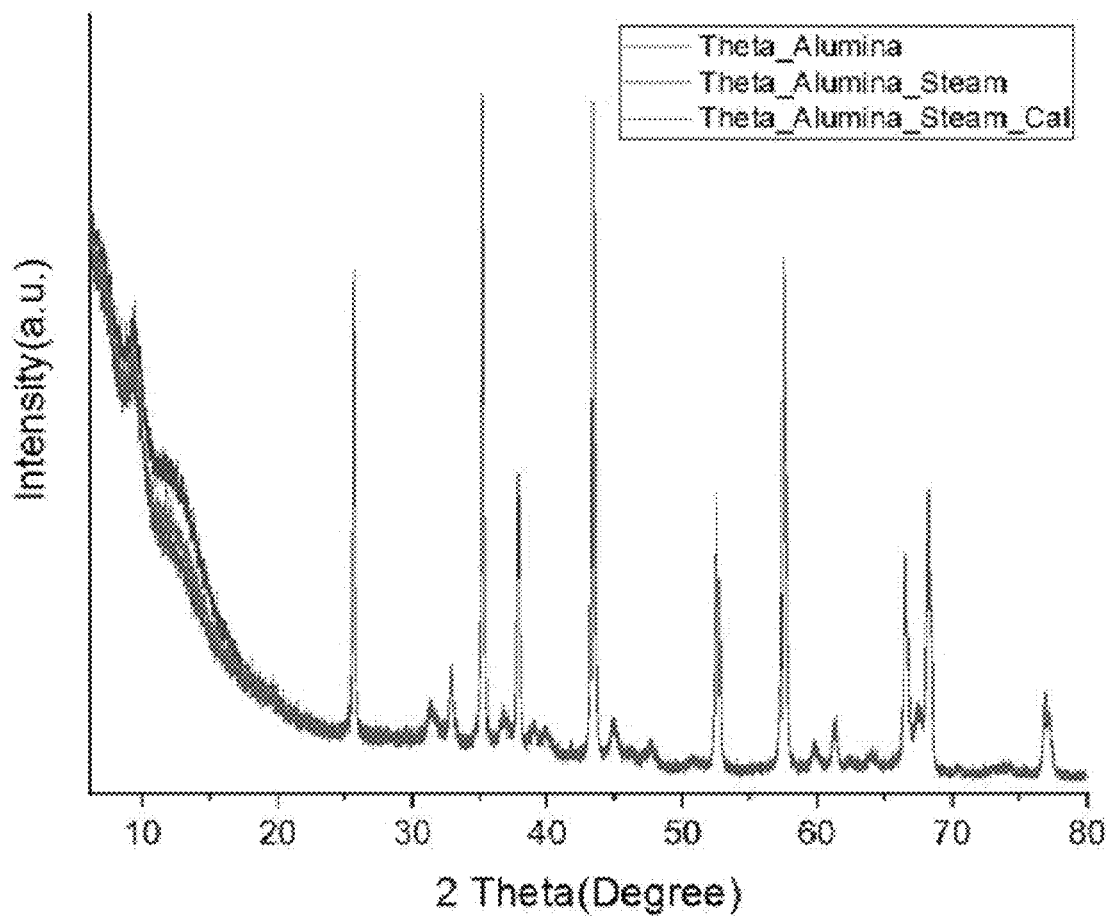

[FIG. 3A] 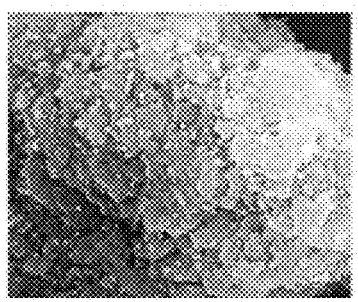 [FIG. 3B] 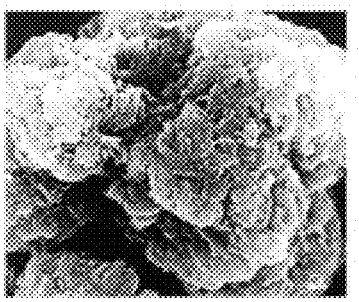 [FIG. 3C] 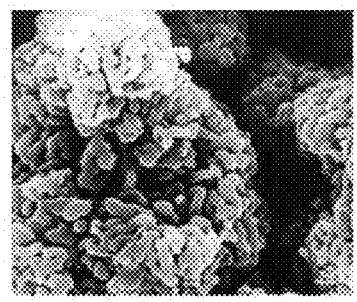
[FIG. 4]
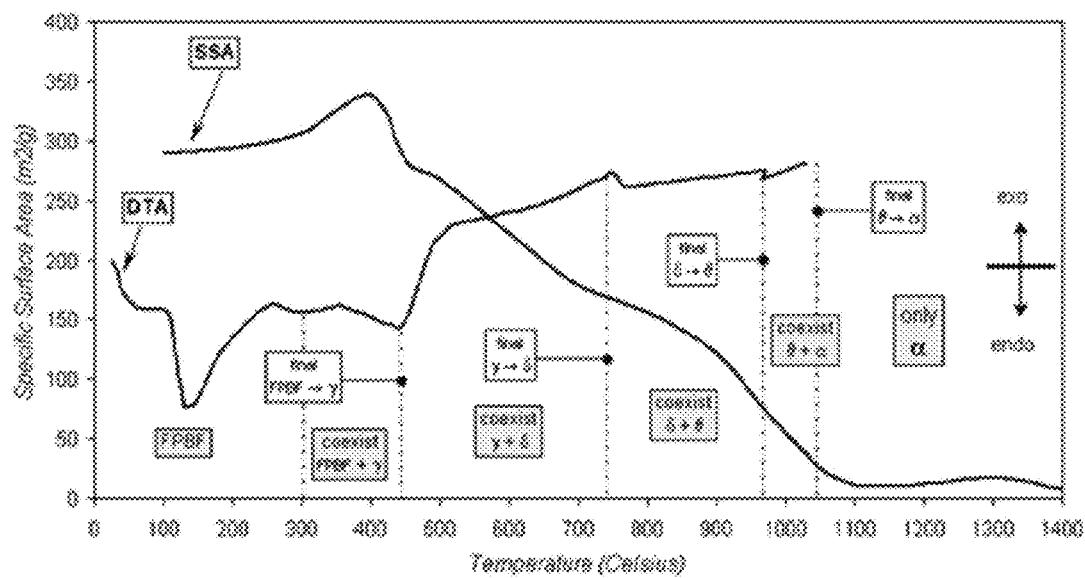

METHOD OF PREPARING ALUMINA CATALYST, ALUMINA CATALYST PREPARED USING SAME, AND METHOD OF PREPARING PROPYLENE USING ALUMINA CATALYST

CROSS-REFERENCE TO RELATED APPLICATIONS

This application is a U.S. national stage of international Application No. PCT/KR2020/016120, filed on Nov. 17, 2020, and claims priority to Korean Patent Application No. 10-2020-0074931, filed on Jun. 19, 2020 in the Korean Intellectual Property Office, the disclosures of which are incorporated herein by reference.

TECHNICAL FIELD

The present invention relates to a method for preparing an alumina catalyst, an alumina catalyst prepared using the method, and a method of preparing propylene using the alumina catalyst. More particularly, the present invention relates to a method of preparing an alumina catalyst that has excellent catalytic activity characterized by high conversion rate for a precursor, high selectivity for a product, and low selectivity for by-products; an alumina catalyst prepared using the method; and a method of preparing propylene using the alumina catalyst.

BACKGROUND

Alumina catalysts, which are used to prepare propylene through dehydration of isopropyl alcohol, are in the form of aluminum oxide, and are used as acid catalysts due to the intrinsic acid sites thereof or as active ingredients such as dispersants for organic/inorganic catalysts due to high stability thereof.

In general, in the case of an alumina catalyst, alumina of various phases (e.g., crystal phase) is obtained through a sintering process using an acid precursor or aluminum hydroxide as a precursor. In this case, as the calcination temperature increases, stable crystal-phase alumina is formed.

Accordingly, when high crushing strength or chemical resistance/corrosion resistance is required in the industry, a stable alumina phase formed through a high-temperature calcination process is used.

Compared to crystal-phase alumina obtained by calcining at a low temperature, crystal-phase alumina obtained by calcining at a high temperature has high stability, but the crystal-phase alumina obtained by calcining at high temperature has problems in that the inherent acid sites of alumina and a large specific surface area as a dispersant are remarkably reduced. Thus, the usefulness of the crystal-phase alumina obtained by a high-temperature calcination process is significantly reduced.

Therefore, there is increasing demand for development of an alumina catalyst having high crushing strength, high chemical resistance/corrosion resistance, and excellent catalytic activity.

SUMMARY

The present invention has been made with a view to address the above problems, and it is an exemplary objective of the present invention to provide a method of preparing an alumina catalyst having high crushing strength, high chemical resistance/corrosion resistance, and excellent catalytic activity.

The above-mentioned objective, and other objectives can be accomplished by the disclosure below.

An exemplary embodiment of this application is a method of preparing an alumina catalyst, the method including: step S1 of performing primary calcination of an alumina precursor at a primary calcination temperature to form mixed-phase alumina including 1% to 15% by weight of alpha-alumina, 60% to 95% by weight of theta-alumina, and 4% to 25% by weight of delta-alumina; step S2 of steam-treating the mixed-phase alumina with water vapor at a stream-treating temperature lower than the primary calcination temperature to activate the mixed-phase alumina and form an activated mixed-phase alumina; and step S3 of performing secondary calcination of the activated mixed-phase alumina after step S2 at a secondary calcination temperature higher than the steam treatment temperature and lower than the primary calcination temperature.

Another exemplary embodiment of this application is a method of preparing an alumina catalyst, the method including: calcining an alumina precursor; performing steam treatment with water vapor after calcining the alumina precursor; and performing burning further calcination step after the steam treatment.

Another exemplary embodiment of this application is a method of preparing an alumina catalyst, the method including: performing primary calcination of an alumina precursor at a primary calcination temperature; performing steam treatment with water vapor at a steam treatment temperature lower than the primary calcination temperature after performing primary calcination; and performing secondary calcination at a secondary calcination temperature higher than the steam treatment temperature and lower than the primary calcination temperature after performing steam treatment.

Another exemplary embodiment of this application is an alumina catalyst prepared by the method described herein.

In accordance with yet another exemplary aspect of the present invention, provided is a method of preparing propylene, the method including dehydrating isopropyl alcohol using the alumina catalyst described herein.

As is apparent from the foregoing, the present invention advantageously provides a method of preparing an alumina catalyst that has excellent catalytic activity characterized by high conversion rate for a precursor, high selectivity for a product, and low selectivity for by-products.

In particular, when propylene is prepared by dehydration of isopropyl alcohol, yield can be increased, and isopropyl alcohol conversion rate and selectivity for propylene can be increased.

In addition, the present invention is directed to a method of preparing an alumina catalyst that has high catalytic activity while at the same time having mechanical strength and corrosion resistance/chemical resistance equal to those of mixed-phase alumina containing an excess of theta-phase alumina.

BRIEF DESCRIPTION OF DRAWINGS

FIG. 1A is a scanning electron microscope (SEM) image of the surface of an alumina catalyst having 70% by weight or more of theta-alumina prepared according to Comparative Example 1.

FIG. 1B is an SEM image of the surface of a steam-treated alumina catalyst prepared according to Comparative Example 2.

FIG. 1C is an SEM image of the surface of an alumina catalyst calcined after steam treatment prepared according to Example 1.

FIG. 2 is a graphical representation of the results of X-ray diffraction (XRD) analysis of catalysts prepared according to the Examples and Comparative Examples.

FIG. 3A is a magnified (100,000×) SEM image of the surface of a catalyst calcined at 700° C.

FIG. 3B is a magnified (100,000×) SEM image of the surface of a catalyst calcined at 1,050° C.

FIG. 3C is a magnified (100,000×) SEM image of the surface of a catalyst calcined at 1,500° C.

FIG. 4 is a graphical representation of the specific surface areas (SSAs) of alumina catalysts as a function of conventional calcination temperatures.

DETAILED DESCRIPTION

Hereinafter, a method of preparing an alumina catalyst, an alumina catalyst prepared using the method, and a method of preparing propylene using the alumina catalyst according to the present invention will be described in detail.

As confirmed by the present inventors, when an alumina catalyst containing an excess of theta-alumina is steam-treated at a specific temperature and then calcined, the surface of the catalyst is activated, and the alumina catalyst has high catalytic activity while having mechanical strength and corrosion resistance/chemical resistance equal to those of conventional theta-alumina. Based on these results, the present inventors conducted further studies.

The method of preparing an alumina catalyst of the present invention includes step S1 of performing primary calcination of an alumina precursor at a primary calcination temperature to form a mixed-phase alumina including 1% to 15% by weight of alpha-alumina, 60% to 95% by weight of theta-alumina, and 4% to 25% by weight of delta-alumina; step S2 of steam-treating the mixed-phase alumina with water vapor at a steam-treating temperature lower than the primary calcination temperature to activate the mixed-phase alumina and form an activated mixed-phase alumina; and step S3 of performing secondary calcination after step S2 at a secondary calcination temperature higher than the steam treatment temperature and lower than the primary calcination temperature. In this case, the stability and activity of an alumina catalyst, which are known to have a trade-off relationship according to temperature, may be improved simultaneously, and an alumina catalyst having high mechanical strength and high corrosion resistance/chemical resistance may be prepared.

Hereinafter, the method of preparing an alumina catalyst of the present invention will be described in detail stepwise.

Mixed-Phase Alumina Formation Step (S1)

For example, in this application, step S1 is a step of performing primary calcination of an alumina precursor to form a mixed-phase alumina including 1% to 15% by weight of alpha-alumina, 60% to 95% by weight of theta-alumina, and 4% to 25% by weight of delta-alumina. In this case, a catalyst having high crushing strength and chemical resistance may be prepared.

Any materials that may be converted into crystal-phase alumina through calcination may be used as the alumina precursor without particular limitation. The alumina precursor is preferably alumina hydrate, more preferably alumina trihydrate, alumina monohydrate, or a mixture thereof.

The alumina trihydrate is preferably gibbsite, bayerite, or a mixture thereof, and the alumina monohydrate is preferably boehmite, diaspore, or a mixture thereof.

For example, the primary calcination temperature may be 900° C. to 1,100° C., preferably 950° C. to 1,100° C., more preferably 1,000° C. to 1,100° C. Within this range, among various crystal phases, mixed-phase alumina containing an excess of theta-alumina may be prepared, and the mechanical strength of the catalyst may be improved.

For example, in step S1, calcination may be performed for 8 to 12 hours, preferably 9 to 11 hours, more preferably 9 to 10 hours. Within this range, structural changes due to heat may be prevented, and excellent mechanical strength may be achieved, thereby increasing resistance to external impact.

For example, the mixed-phase alumina formed in step S1 may include 1% to 15% by weight of alpha-alumina, 60% to 95% by weight of theta-alumina, and 4% to 25% by weight of delta-alumina.

For example, the mixed-phase alumina may not include gamma-alumina. In this case, a catalyst having high crushing strength and chemical resistance may be prepared.

In this application, the absence of gamma-alumina means that the content of gamma-alumina is less than 0.5% by weight, preferably 0.1% by weight or less, more preferably 0.01% by weight or less. Specifically, the absence of gamma-alumina means that no gamma-alumina is detected by XRD analysis when analyzing the mixed-phase alumina of this application.

In addition, the mixed-phase alumina may include 1% to 15% by weight of alpha-alumina, 60% to 95% by weight of theta-alumina, 4% to 25% by weight of delta-alumina, and 0% by weight of gamma-alumina. In this case, an alumina catalyst having excellent catalytic activity may be prepared.

In one exemplary embodiment, in the mixed-phase alumina, based on 100% by weight of the mixed-phase alumina, alpha-alumina may be included in an amount of 1% to 15% by weight, preferably 5% to 15% by weight, more preferably 10% to 15% by weight. Within this range, catalytic activity may be improved.

In another exemplary embodiment, in the mixed-phase alumina, based on 100% by weight of the mixed-phase alumina, theta-alumina may be included in an amount of 60% to 95% by weight, preferably 60% to 90% by weight, more preferably 60% to 80% by weight. Within this range, a catalyst having excellent mechanical strength can be prepared, which prevents the catalyst from being broken during regeneration or catalyst circulation.

In another exemplary embodiment, in the mixed-phase alumina, based on 100% by weight of the mixed-phase alumina, delta-alumina may be included in an amount of 4% to 25% by weight, preferably 4% to 20% by weight, more preferably 10% to 20% by weight. Within this range, excellent mechanical strength may be achieved, thereby increasing resistance to external impact.

In this application, when the weights of alpha-alumina, theta-alumina, delta-alumina, and gamma-alumina are measured, an XRD graph is obtained at 10 to 80° (step: 0.05°, measurement time per step: 1 s) using an X-ray diffraction analyzer (Bruker Co.) having Cu radiation (30 kV, 10 mA). Then, based on the XRD analysis data, a structure is analyzed through Rietveld refinement to calculate content ratio.

Activation Step (S2)

For example, in this specification, step S2 is a step of steam-treating the mixed-phase alumina with water vapor at a steam-treating temperature lower than the primary calcination temperature to activate the mixed-phase alumina. In this application, steam treatment refers to supply of water vapor (steam) using nitrogen as a carrier gas into a reactor set to a specific temperature.

For example, the steam treatment may refer to supply of water vapor and nitrogen into a reactor in the presence of the mixed-phase alumina.

For example, the mixing ratio of nitrogen to water vapor (the volume ratio of $N_2:H_2O$) is preferably 1,500:1 to 10,000:1, more preferably 2,000:1 to 3,000:1. Within this range, catalytic activity may be improved while maintaining excellent mechanical strength and chemical resistance.

In addition, the mixing ratio of the mixed-phase alumina to water vapor (the weight ratio of the mixed-phase alumina to water vapor) is preferably 1:0.01 to 1:100. As another example, based on 75 g of the mixed-phase alumina, water vapor ($H_2O$) may be fed at a rate of 0.026 to 0.1 g/min. Within this range, high mechanical strength and high corrosion resistance/chemical resistance may be achieved, and thus an alumina catalyst having high stability and activity may be prepared.

For example, the stream-treating temperature may be lower than the primary calcination temperature. Preferably, the steam-treating temperature is lower than the secondary calcination temperature to be described below.

For example, the steam-treating temperature may be a temperature inside a reactor. As an example, the steam-treating temperature may be 200° C. to 500° C., preferably 300° C. to 450° C. Within this range, in the secondary calcination step to be described later, activation that is optimized for calcination may be achieved.

For example, step S2 may be a step of performing steam treatment for 1 to 10 hours, preferably 3 to 6 hours. Within this range, high mechanical strength and high corrosion resistance/chemical resistance may be achieved, and thus an alumina catalyst having high stability and activity may be prepared.

Calcination Step (S3)

For example, in this application, step S3 is a step of calcining the mixed-phase alumina activated in step S2 at a secondary calcination temperature.

For example, the secondary calcination temperature may be a temperature higher than the steam-treating temperature and lower than the primary calcination temperature.

For example, the secondary calcination temperature may be greater than 500° C. and less than or equal to 600° C., preferably greater than 500° C. and less than or equal to 580° C., more preferably 520° C. to 580° C. Within this range, the catalytic activity and stability of the mixed-phase alumina activated in step S2 may be improved.

For example, step S3 may be a step of performing calcination for 3 to 7 hours, preferably 3 to 6 hours, more preferably 4 to 6 hours. Within this range, an alumina catalyst having high conversion rate for a precursor, high selectivity for a product, and low selectivity for by-products may be prepared.

The alumina catalyst of the present invention is a catalyst with improved stability and catalytic activity, and is different from mixed-phase alumina before undergoing activation processes such as steam treatment (step S2) and calcination (step S3). The alumina catalyst of the present invention may have high catalytic activity while at the same time having mechanical strength and corrosion resistance/chemical resistance equal to those of mixed-phase alumina before the activation processes, i.e., mixed-phase alumina containing an excess of theta-phase alumina. In particular, the catalyst has an advantage of being able to work at high temperatures.

In addition, the alumina catalyst may be a catalyst that exhibits the characteristics of theta-phase alumina while the surface thereof exhibits the characteristics of gamma-phase alumina. Accordingly, the alumina catalyst may have a large specific surface area at high temperatures, and thus the alumina catalyst may have excellent catalytic activity.

It is generally known that in the catalytic activity decreases in the order of gamma-alumina, delta-alumina, theta-alumina, and alpha-alumina, but the strength of the catalyst increases. That is, it is known that the activity and strength of the catalyst are inversely proportional. However, unexpectedly the alumina catalyst of the present invention simultaneously achieves the high strength of theta-alumina and high activity of gamma-alumina.

For example, the alumina catalyst may be prepared by the method of preparing an alumina catalyst of the present invention as described above.

For example, the alumina catalyst may be a catalyst for isopropyl alcohol dehydration.

For example, the alumina catalyst may have a specific surface area of 30 m$^2$/g or more, preferably 35 m$^2$/g or more, more preferably 35 m$^2$/g to 85 m$^2$/g. Within this range, excellent catalytic activity may be achieved.

In this application, for example, the specific surface area may be obtained by measuring the adsorption/desorption amount of nitrogen according to a partial pressure ($0.10<p/p_0<0.25$) using a BELSORP-mini II (Mictrotrac-BEL Co.).

For example, the alumina catalyst may have a pore volume of 0.60 cm$^3$/g or less, preferably 0.45 cm$^3$/g to 0.55 cm$^3$/g. Within this range, catalytic activity may be excellent.

In this application, for example, the pore volume may be calculated using an adsorption amount at a partial pressure ($p/p_0$) of 0.99 using a BELSORP-mini II (Mictrotrac-BEL Co.).

For example, the alumina catalyst may be supported with an active ingredient and may have high degree of dispersion.

Any loading methods commonly used in the art to which the present invention pertains may be used in the present invention without particular limitation.

For example, the active ingredient may include one or more selected from the group consisting of platinum, tin, germanium, gallium, indium, strontium, and manganese.

For example, the alumina catalyst may include a halogen component in an amount of 0.5% by weight or less, or 0.1% to 0.4% by weight. In this case, catalytic activity may be improved.

The halogen component, preferably chlorine, is combined with the aluminum element of an alumina catalyst to weaken the properties of the Lewis acids of the alumina, thereby facilitating desorption of a product and suppressing formation of by-products.

In this specification, halogen components may be measured using an inductively coupled plasma (ICP) method.

For example, the alumina catalyst may have an isopropyl alcohol (IPA) conversion rate of 60% to 100%, preferably 60% to 90%, more preferably 60% to 80%. Within this range, process efficiency may be improved.

For example, the alumina catalyst may have a propylene selectivity of 90% or more, preferably 90% to 100%. Within this range, process efficiency may be improved.

For example, the alumina catalyst may have a selectivity of 10% or less, preferably 9.6% or less, more preferably 1% to 9.57% for by-products having 3 or more carbon atoms. Within this range, the efficiency of a rear-end separation process may be improved.

In this specification, the by-products having 3 or more carbon atoms may be compounds having 3 or more carbon atoms, e.g., diisopropyl ether (DIPE).

In addition, the isopropyl alcohol (IPA) conversion rate, the propylene selectivity, and the selectivity for by-products having 3 or more carbon atoms may be obtained by analyzing the amounts of various components of a composition (product) using gas chromatography.

In this application, the rear-end separation process is a process of separating water and by-products generated during dehydration. Specifically, the rear-end separation process is a process of liquefying DIPE, which is a by-product, by lowering the temperature at the rear-end of a reactor to separate water and the by-product. Accordingly, as by-products decrease in the rear-end separation process, separation efficiency increases.

For example, the catalyst of the present invention may be used to dehydrate isopropyl alcohol to prepare propylene. Hereinafter, the dehydration of the present invention will be described.

For example, the method of preparing propylene may be performed by dehydrating isopropyl alcohol in the presence of the above-described alumina catalyst.

For example, the dehydration may be performed by passing isopropyl alcohol through a reactor filled with the alumina catalyst of the present invention.

As an example, the dehydration may include a step of filling a reactor with the catalyst of the present invention; and a step of continuously passing isopropyl alcohol through the reactor filled with the catalyst to perform dehydration.

Any reactors commonly used in the art to which the present invention pertains may be used as the reactor of the present invention without particular limitation. For example, a metal tube reactor, a multi-tubular reactor, or a plate-type reactor may be used.

For example, based on a total volume inside a reactor, the catalyst may be included in an amount of 10% to 50% by volume or 10% to 25% by volume.

For example, the dehydration may be performed at 200° C. to 500° C., preferably 250° C. to 400° C. Within this range, excellent reaction efficiency may be achieved without excessive energy consumption, thereby increasing productivity for propylene.

Hereinafter, the present invention will be described in more detail in the following preferred examples. However, these examples are provided for illustrative purposes only and should not be construed as limiting the scope and spirit of the present invention. In addition, it will be apparent to those skilled in the art that various changes and modifications may be made without departing from the spirit and scope of the present invention, and such changes and modifications are also within the scope of the appended claims.

EXAMPLES

Example 1

Boehmite was subjected to calcination at 1,100° C. under an air atmosphere for 10 hours to obtain mixed-phase alumina including 10% by weight of alpha-alumina, 70% by weight of theta-alumina, and 20% by weight of delta-alumina, a tubular reactor was filled with the mixed-phase alumina, the temperature of the tubular reactor was set to 400° C., and then steam treatment was performed by supplying water vapor and nitrogen into the reactor for 3 hours. At this time, water vapor was supplied at a rate of 0.026 g/min to 0.1 g/min using an HPLC pump, nitrogen was supplied at a rate of 133 ml/min using a mass flow controller (MFC), the mixing ratio of nitrogen to water vapor (the volume ratio of $N_2:H_2O$) was 2,500:1, and the weight ratio of water vapor to the mixed-phase alumina was 0.01 to 100:1. In addition, after steam treatment, calcination was performed at 550° C. for 5 hours to obtain an alumina catalyst.

Example 2

The process was performed in the same manner as in Example 1, except that water vapor and nitrogen were supplied for 6 hours instead of 3 hours during steam treatment.

Comparative Example 1

Boehmite was subjected to calcination at 1,100° C. under an air atmosphere for 10 hours to obtain a mixed-phase alumina. At this time, the obtained mixed-phase alumina included 10% by weight of alpha-alumina, 70% by weight of theta-alumina, 20% by weight of delta-alumina, and 0% by weight of gamma-alumina.

Comparative Example 2

The process was performed in the same manner as in Example 1, except that the step of performing calcination at 550° C. for 5 hours was omitted.

TEST EXAMPLES

The properties of catalysts prepared according to Examples 1 and 2 and Comparative Examples 1 and 2 were measured according to the following methods, and the results are shown in Table 1 and FIGS. 1A to 1C and 2.

Test Example 1: Evaluation of Catalytic Activity

The catalytic activities of the prepared catalysts were evaluated by using the prepared catalysts in the process of preparing propylene by the dehydration of isopropyl alcohol (IPA).

Specifically, 0.75 g of the prepared catalyst was placed in a 1 inch fixed-bed reactor, and reaction was performed by passing isopropyl alcohol through the reactor at a rate of 0.01 g/min to 0.1 g/min.

At this time, the conditions of the fixed-bed reactor were set as follows: a pressure of 20 atm; a reaction temperature of 300° C.; and a WHSV (Weight Hour Space Velocity) of 2.0 $h^{-1}$ to 2.5 $h^{-1}$. The contents of the components of a composition (product) were analyzed 6 hours after an IPA dehydration test using a gas chromatograph connected to the reactor. Based on the analysis results, IPA conversion rate, propylene selectivity, and selectivity for by-products having 3 or more carbon atoms (diisopropyl ether; DIPE) were calculated, and the results are shown in Table 1 below. Here, a gas chromatograph (model name: Agilent 7890B GC, column: HP-1 (100 m×250 μm×0.5 μm), Agilent Co.) was used, and analysis conditions were as follows. Carrier gas: helium (flow rate of 1 mL/min), detector: F.I.D, sampling loop volume: 1 mL (split ratio of 50:1), and heating mode: 50° C./10 min→100° C./0 min (temperature rise at 5° C./min)→200° C./0 min (temperature rise at 10° C./min). In this case, 0 min means not staying at the corresponding temperature.

TABLE 1

| Classification | IPA conversion rate (%) | Propylene selectivity (%) | C3 ≤ by-products (%) |
| --- | --- | --- | --- |
| Example 1 | 61.4 | 91.9 | <7.93 |
| Example 2 | 60.9 | 90.2 | <9.57 |
| Comparative Example 1 | 35.3 | 82.0 | <17.5 |
| Comparative Example 2 | 54.5 | 89.4 | <10.35 |

As shown in Table 1, in the case of Examples 1 and 2, through the activation process (steam treatment and calcination), IPA conversion rate and propylene selectivity increase, and selectivity for by-products having 3 or more carbon atoms decreases.

On the other hand, in the case of Comparative Example 1 corresponding to conventional theta-phase alumina, a catalyst not processed by the activation process of the present invention was prepared. When the catalyst of Comparative Example 1 was used, catalytic activity was significantly reduced compared to Examples 1 and 2.

In addition, the catalyst of Comparative Example 2 prepared by a process in which steam treatment was additionally performed to Comparative Example 1 exhibited lower activity than the catalysts of Examples 1 and 2 prepared by a process in which calcination was additionally performed after steam treatment.

Test Example 2: Surface Property Evaluation

SEM images were used to confirm changes in the physical properties of the surface of the prepared catalyst.

The SEM images of FIGS. 3A to 3C were obtained by photographing the surface of an alumina precursor after the alumina precursor was subjected to primary calcination at 700° C. (FIG. 3A), 1,050° C. (FIG. 3B), or 1,500° C. (FIG. 3C) (see Structure, Surface Area and Morphology of Aluminas from thermal decomposition of Al(OH) (CH₃COO)₂ Crystals, An. Acad. Bras. Cienc., 72, (2000), pp. 471-495), and FIG. 4 is a graphical representation of the specific surface areas according to calcination temperatures (see Specific surface area and structures of aluminas from fibrillar pseudoboehmite, Revista Materia, 13 (2) (2008), pp. 329-341). Based on FIGS. 3A to 3C and 4, in general, as temperature increases, alumina particles aggregate, thereby reducing the surface area of the catalyst. In this case, decrease in the surface area means that the activity of the catalyst decreases.

However, in the case of the catalyst of the present invention, although primary calcination was performed at high temperatures, the specific surface area of the catalyst did not decrease, but rather increased.

Additionally, FIG. 1A is an SEM image showing a catalyst containing an excess of theta-alumina according to related art, and particles are aggregated due to high-temperature calcination, thereby increasing density and reducing a specific surface area. On the other hand, in the SEM image of FIG. 1B showing a steam-treated catalyst, there are relatively few aggregated particles compared to FIG. 1A, and small particles are generated on the surface, indicating that specific surface area has increased.

In addition, in the SEM image of FIG. 1C showing a catalyst burned after steam treatment, a specific surface area increases compared to FIGS. 1A to 1B, indicating that gamma-phase alumina is properly formed on the surface of the catalyst.

Test Example 3: Evaluation of Crystal Structure of Catalyst

The crystal structure of the prepared alumina catalyst was analyzed through X-ray diffraction (XRD), and the results are shown in FIG. 2.

Based on the XRD analysis results in FIG. 2, it can be confirmed that the crystal structures of the alumina catalysts prepared in Example 1 and Comparative Examples 1 and 2 exhibit theta-phase properties.

That is, the alumina catalyst of the present invention exhibits theta-phase properties, and high catalytic activity due to surface modification through steam treatment and calcination.

In summary, in the case of the alumina catalyst prepared by the preparation method of the present invention, the crystal structure thereof was not changed significantly, and the surface physical properties thereof were changed. The alumina catalyst of the present invention had excellent stability and catalytic activity due to surface change while having mechanical strength and corrosion resistance/chemical resistance equal to those of a conventional alumina catalyst containing an excess of a theta phase.

The invention claimed is:

1. A method of preparing an alumina catalyst comprising the steps of:
    performing primary calcination of an alumina precursor at a primary calcination temperature to form a mixed-phase alumina comprising 1% to 15% by weight of alpha-alumina, 60% to 95% by weight of theta-alumina, and 4% to 25% by weight of delta-alumina;
    steam-treating the mixed-phase alumina with water vapor at a steam-treating temperature lower than the primary calcination temperature to form activated mixed-phase alumina, wherein the steam-treating temperature is 200° C. to 500° C.; and
    performing secondary calcination of the activated mixed-phase alumina at a temperature higher than the steam-treating temperature and lower than the primary calcination temperature, wherein the secondary calcination temperature is of greater than 500° C. and less than or equal to 600° C.

2. The method according to claim 1, wherein the primary calcination temperature is 900° C. to 1,100° C.

3. The method according to claim 1, wherein the primary calcination is performed for 8 hours to 12 hours.

4. The method according to claim 1, wherein the steam-treating is performed for 1 hour to 10 hours.

5. The method according to claim 1, wherein the secondary calcination is performed for 3 hours to 7 hours.

6. The method according to claim 1, wherein the mixed-phase alumina does not comprise gamma-alumina.

7. The method according to claim 1, wherein the alumina precursor comprises one or more selected from gibbsite, bayerite, boehmite, and diaspore.

8. The method according to claim 1, wherein the alumina catalyst is a catalyst for isopropyl alcohol dehydration.

9. An alumina catalyst prepared by the method according to claim 1.

10. A method of preparing propylene comprising a step of dehydrating isopropyl alcohol using the alumina catalyst according to claim 9.

* * * * *